(12) United States Patent
Venkatasubramanian

(10) Patent No.: US 9,326,850 B2
(45) Date of Patent: May 3, 2016

(54) SUTURELESS PROSTHETIC DEVICE

(71) Applicant: St. Jude Medical, Cardiology Division, Inc., St. Paul, MN (US)

(72) Inventor: Ramji T. Venkatasubramanian, Maple Grove, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 86 days.

(21) Appl. No.: 14/173,153

(22) Filed: Feb. 5, 2014

(65) Prior Publication Data

US 2014/0243964 A1    Aug. 28, 2014

Related U.S. Application Data

(60) Provisional application No. 61/768,793, filed on Feb. 25, 2013.

(51) Int. Cl.
  *A61F 2/06*   (2013.01)
  *A61F 2/24*   (2006.01)
(52) U.S. Cl.
  CPC ............. *A61F 2/2418* (2013.01); *A61F 2/2412* (2013.01)

(58) Field of Classification Search
  CPC .............................. A61F 2/2418; A61F 2/2409
  See application file for complete search history.

(56) References Cited

U.S. PATENT DOCUMENTS 8,500,798 B2 *   8/2013   Rowe et al. .................... 623/2.1

* cited by examiner

*Primary Examiner* — Thomas J Sweet
*Assistant Examiner* — Brian Dukert
(74) *Attorney, Agent, or Firm* — Lerner, David, Littenberg, Krumholz & Mentlik, LLP

(57) ABSTRACT

A prosthetic device for use in an anatomical orifice or lumen of a patient includes an expandable first stent structure coupled to a valve support structure having at least one leaflet. The stent structure includes a collar provided with at least one groove or opening adapted to engage a tab extending from the valve support structure. Rotation of the stent structure and valve support structure relative to one another assembles the prosthetic valve device. The prosthetic valve device may be used for sutureless treatment of various valvular conditions such as aorta stenosis and mitral valve replacement.

17 Claims, 4 Drawing Sheets

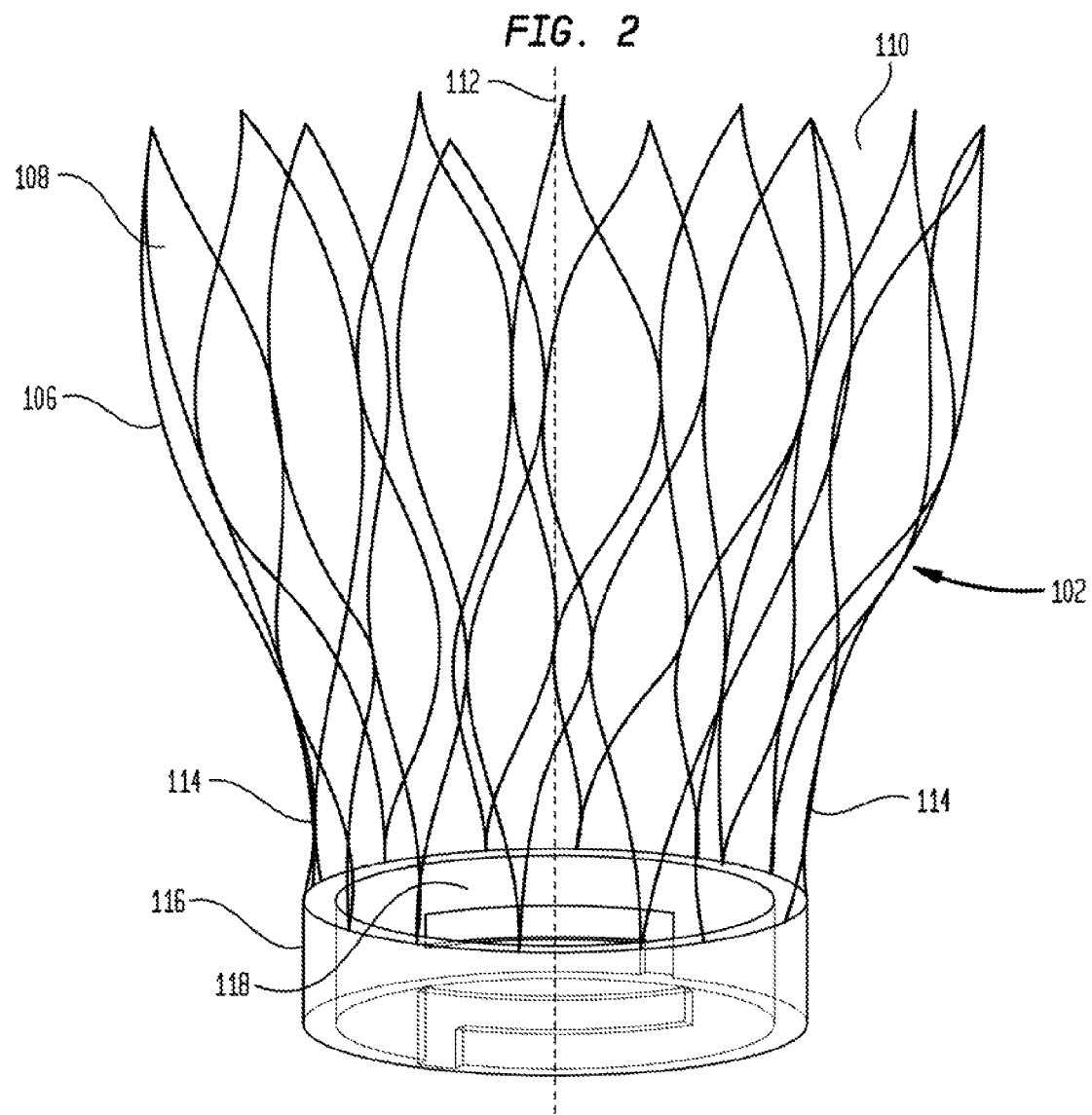
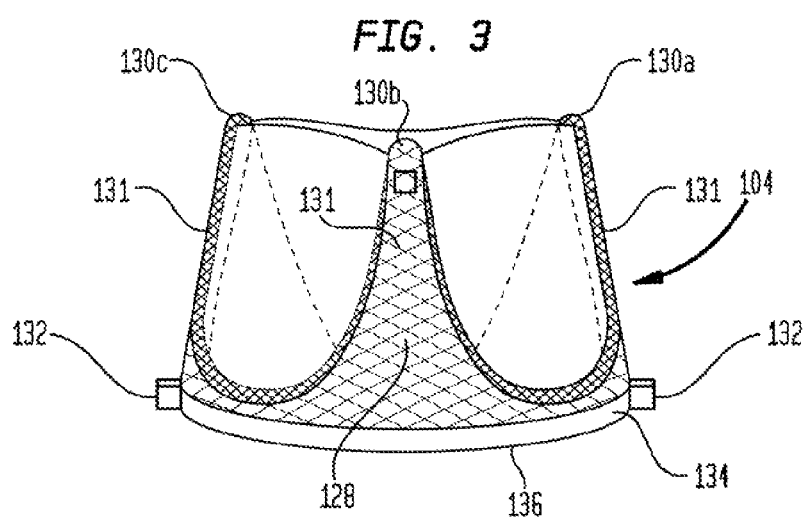

SUTURELESS PROSTHETIC DEVICE

CROSS-REFERENCE TO RELATED APPLICATIONS

The present application claims the benefit of the filing date of U.S. Provisional Patent Application No. 61/768,793 filed Feb. 25, 2013, the disclosure of which is hereby incorporated herein by reference.

BACKGROUND OF THE INVENTION

The present disclosure is related generally to sutureless prosthetic devices such as for native heart valve replacements, and more particularly, to devices, systems and methods for treatment of valvular diseases such as aortic stenosis using a sutureless prosthetic heart valve.

Aortic stenosis is a condition where the aortic valve becomes more narrow and does not open fully, leading to increased pressure within the left ventricle, as well as decreased blood flow from the heart. Such a condition may lead to shortness of breath, due to blood backing up in the lungs, as well as light-headedness and fainting, due to insufficient blood flow from the heart to the brain and rest of the body. Aortic stenosis is one of the most common valvular diseases, affecting 2-4% of adults over the age of 65 in the United States.

Aortic stenosis is typically treated by replacement of the aortic valve via open heart surgery. During open heart surgery, the patient is placed on cardiopulmonary bypass to maintain blood flow through the body while the surgery on the heart is performed. It is commonly understood that many risks associated with open heart surgery are directly related to the time the patient spends on bypass, and thus, the longer the time spent on bypass, the greater the risk of complications during the surgery. Moreover, due to this correlation, many patients are believed to be left untreated.

A recent trend, as an alternative to open heart surgery, aims to implant a replacement valve through a catheter, thereby eliminating the need for any bypass. Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. One type of stent on which the valve structures are ordinarily mounted is a self-expanding stent. To place such a valve into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. The self-expanding stent automatically begins to expand as the sheath covering the valve is withdrawn. Once the self-expanding valve has been fully deployed, it expands to a diameter larger than that of the sheath that previously contained the valve in the collapsed condition.

While collapsible prosthetic heart valves avoid the risks associated with open heart surgery, there remains unanswered issues regarding the longevity of the prosthetic heart valves compared to those implanted via open heart surgery. Further, it is commonly understood that the collapsible design feature of the valve limits the leaflet thickness and leaflet profile of the valve thereby limiting the maximum durability that can be achieved through a collapsible valve. There therefore is a need for improvements to the devices, systems and methods for sutureless prosthetic heart valves when treating valvular diseases which require cardiopulmonary bypass, by way of example, aortic stenosis.

BRIEF SUMMARY OF THE INVENTION

The present disclosure relates in general to prosthetic heart valves of the sutureless type intended to minimize cardiopulmonary bypass time during open heart surgery. However, the present disclosure also relates to prosthetic devices for use in an anatomical orifice or lumen of a patient where the conditions of stenosis may be present. More particularly, a sutureless bovine pericardial tissue heart valve is disclosed that can be implanted during open heart surgery while the patient is placed on a cardiopulmonary bypass in a manner which minimizes the time the patient is spent on the bypass. The sutureless prosthetic heart valve generally includes two stent frameworks that are deployed separately. An outer, self-expanding stent constructed from material such as nitinol is provided with a collar which includes an engagement member receiving opening. The second generally non-expandable inner stent is formed from, for example, a titanium framework which supports the heart valve. In one embodiment, the heart valve is constructed from three leaflets made from processed porcine and/or bovine tissue. The outer self-expanding stent may be deployed from the aortic side. The native valve leaflets may be removed, however, the outer stent may be positioned in the aortic valve in a manner which keeps the native valve open at all times. The inner stent is subsequently positioned into the interior of the outer stent and locked therein by an engagement member received within the engagement member receiving opening within the collar.

In accordance with one embodiment of the present disclosure, there is described a prosthetic device for use in an anatomical orifice or lumen of a patient, the device comprising a first stent structure defining an interior region and having a collar at one end thereof; a valve support structure adapted to be secured to the collar within the interior region of the first stent structure; and a valve structure coupled to the valve support structure.

In accordance with another embodiment of the disclosure, there is described a prosthetic device for use in an anatomical orifice or lumen of a patient, the device comprising a first stent structure defining an interior region having a longitudinal axis, the first stent structure including a collar, the collar having at least one engagement member receiving structure; and a second stent structure having at least one engagement member adapted to be received within the engagement member receiving structure of the first stent structure for releasably securing the second stent structure to the first stent structure within the interior region.

In accordance with another embodiment of the present disclosure, there is described a prosthetic heart valve device comprising a first stent structure defining a first interior region about a longitudinal axis, the first stent structure including a collar surrounding one end of the first stent structure, the collar including a first groove extending longitudinally to an edge of the collar in communication with a second groove extending circumferentially about the collar, wherein the first stent structure is configured to be expandable from a collapsed state to an expanded state; a second stent structure defining a second interior region, the second stent structure supporting a heart valve structure having at least one leaflet arranged within the second interior region, the second stent structure including a base having at least one tab extending radially outward therefrom; wherein the second stent structure is configured to be received within the first interior region of the first stent structure with the base juxtaposing the collar; and wherein the second stent structure is securable to the first stent structure by initially receiving the at least one tab within the first groove, and then, within the second groove of the collar by rotation of the first and second stent structures relative to one another.

In accordance with another embodiment of the present disclosure, there is described a method for assembling a prosthetic valve device for use in an anatomical orifice or lumen of a patient, the method comprising arranging a valve support structure including a valve having at least one leaflet within an expandable first stent structure, the expandable first stent structure configured to be attached at a native site of an anatomical orifice or lumen of a patient; and securing the value support structure to the first stent structure.

In accordance with another embodiment of the present disclosure, there is described a prosthetic device for use in an anatomical orifice or lumen of a patient, the device comprising a first structure defining a first interior region expandable from a collapsed configuration to an expanded configuration, the first structure having a collar at an end thereof, and a second structure defining a second interior region, the second structure having a portion configured to be secured to the collar when the second structure is received within the first interior region when the first structure is in the expanded configuration.

BRIEF DESCRIPTION OF THE DRAWINGS

Various embodiments of the present disclosure will now be described with reference to the appended drawings. It is appreciated that these drawings depict only exemplary embodiments of the disclosure and are therefore not to be considered limiting of its scope.

FIG. 2 is a perspective view illustrating one embodiment of the self-expanding stent having a collar at one end thereof as illustrated in FIG. 1.

FIG. 3 is a perspective view of a second stent structure supporting a heart valve including one or more leaflets as illustrated in FIG. 1.

DETAILED DESCRIPTION

Figure 1:
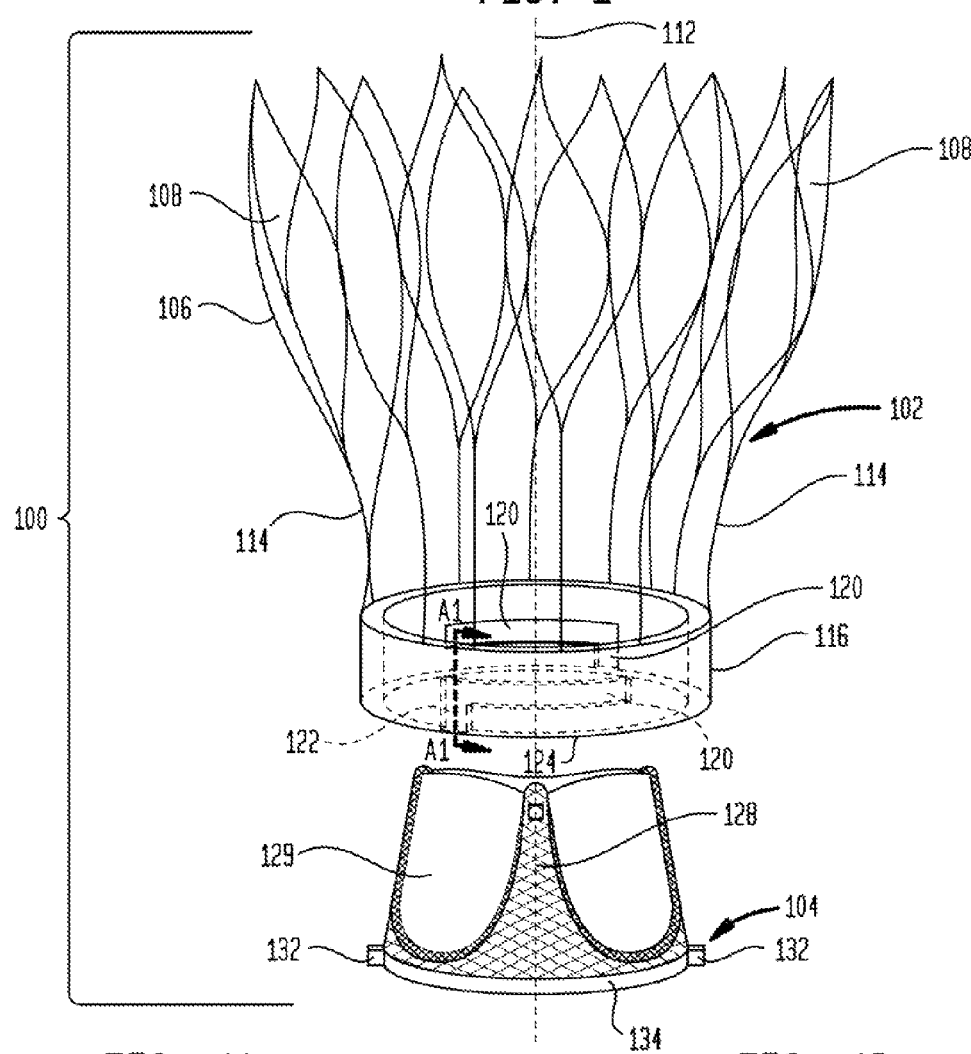
FIG. 1 illustrates a perspective view of one embodiment of a sutureless prosthetic heart valve in unassembled relationship in accordance with the present disclosure.

As may be used herein, the term "proximal," when used in connection with a prosthetic heart valve, refers to the end of the heart valve closest to the heart when the heart valve is implanted in a patient, whereas the term "distal," when used in connection with a prosthetic heart valve, refers to the end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

In describing the preferred embodiments of the disclosure illustrated in the drawings, specific terminology will be used for the sake of clarity. However, the invention is not intended to be limited to the specific terms so used, and it is to be understood that each specific term includes all equivalents that operate in a similar manner to accomplish a similar purpose.

In accordance with one embodiment, there is illustrated in FIG. 1 a sutureless prosthetic heart valve device 100 used for replacement of a damaged or otherwise malfunctioning heart valve, such as a result of aortic stenosis. The prosthetic heart valve device 100 may be implanted into a patient suffering from a malfunctioning heart valve through open heart surgery procedures. However, it is to be understood that the prosthetic heart device 100 can be used more broadly in controlling bodily fluid flow through an anatomical orifice or lumen of a patient or other cardiac valves. In this regard, it is also contemplated that the prosthetic heart valve device 100 is suitable for use in mitral valve repair such as replacement of the native heart valve where mitral valve prolapse exists. Still further, it is to be understood that a similarily constructed device may be used in other anatomical orifices or lumens of a patient, where for example, stenosis conditions may be present.

The prosthetic heart valve device 100 includes a first stent structure 102 and a second stent structure 104 adapted to be coupled together in removable assembled relationship. As best shown in FIGS. 1 and 2, the stent structure 102 may have an annular section 106 which includes a plurality of cells 108 connected to one another around the stent structure. The stent structure 102 may include one or more annular rows of cells 108 connected circumferentially to define an interior region 110. The cells 108 define the interior region 110 about a longitudinal axis 112. When the stent structure 102 is in the expanded condition as shown, each cell 108 may be substantially diamond shaped. Regardless of its shape, each cell 108 may be formed from a plurality of elongated struts 114.

The stent structure 102, in accordance with the preferred embodiment, is formed as an expandable stent, and more preferably a self-expanding stent, which includes a collar 116 attached to the free ends of the struts 114. It is to be understood that the stent structure 102, could also be a balloon expandable stent framework in which case other materials such as stainless steel could also be used. The struts 114 which form the annular section 106 and the cells 108 can be constructed of elastic like material, such as nitinol, which may self-expand from a compressed state back to its original, expanded state. Such self-expanding stent structures are well known in the art. More specifically, the stent structure 102 may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides.

The collar 116 which may be formed of similar materials includes a throughbore 118 to allow passage of blood therethrough, as well as for placement of the second stent structure 104 therein. The longitudinal axis 112 passes through the throughbore of collar 116. The collar may also include a securement structure for the second stent 104, such as, for example, an engagement member receiving structure for releasably engaging with a portion of the second stent structure.

Figure 1A:
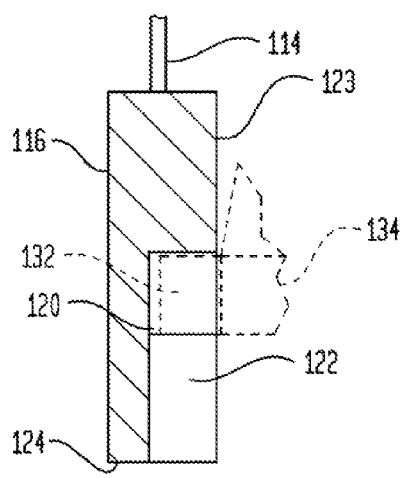
FIG. 1A is a cross-sectional view taken along line 1A-1A in FIG. 1 illustrating one embodiment of an engagement member receiving opening.
Figure 1B:
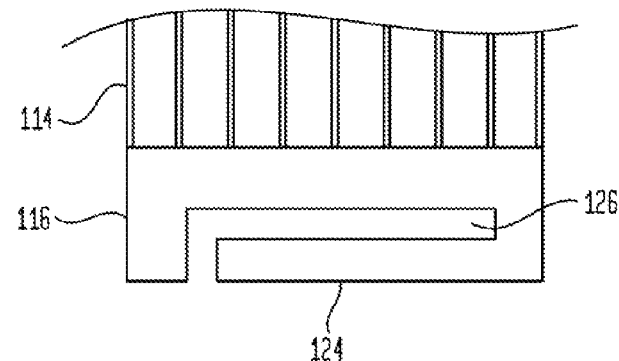
FIG. 1B is a side elevation view of another embodiment of an engagement member receiving opening.

In accordance with one embodiment, the engagement member receiving structure may include at least one circumferentially arranged first recessed groove 120 and at least one longitudinally arranged second recessed groove 122 both formed within the inner surface 123 of the collar as best shown in FIG. 1A. The first and second grooves are in communication with each other, having a general "L" shape. The first groove 120 is provided within the inner surface 123 of the collar extending in a generally circumferential direction around the longitudinal axis 112 at least partially encircling the collar 116, generally in a plane perpendicular to the longitudinal axis. The second groove 122 is arranged generally parallel to the longitudinal axis 112 in an axial direction having one end terminating in communication with the first groove 120 and its other end terminating along the edge 124 of the collar 116. In another embodiment as shown in FIG. 1B, the first and second grooves 120, 122 may extend entirely through the wall of the collar 116 as a cut out portion, thereby forming a continuous L-shaped opening 126 in communication with the edge 124 of the collar.

In the preferred embodiment, it is contemplated that a plurality of the aforementioned engagement member receiving structures may be provided in the collar 116 at locations circumferentially about the collar, although only one such structure is contemplated. In the embodiment illustrated, a pair of engagement member receiving structures is arranged circumferentially opposing one another within the collar 116. However, it is contemplated that additional engagement member receiving structures each formed of the first and second grooves 120, 122 or opening 126 may be provided within the collar at equally spaced or randomly spaced apart locations.

Referring to FIG. 3, the second stent structure 104 includes a stent portion 128 for supporting a replacement valve 129 including at least one leaflet 130a. In the illustrated embodiment of FIG. 3, the replacement valve 129 includes three leaflets 130a, 130b, 130c and may be used as a tricuspid valve such as an aortic valve. Of course, other leaflet configurations are envisioned such that the present invention may be used to replace other types of heart valves such as mitral valves. The leaflets 130 may be constructed of animal tissue, such as processed bovine and/or processed porcine pericardial tissue, or the like. Other artificial materials such as polymers such as polyurethane, as well as biopolymers, including but not limited to, collagen or fibrin based tissue engineered materials may also be used to construct the leaflets.

The stent portion 128 may be rigid, expandable or self-expandable, and may be constructed as discussed with respect to the first stent structure 102 using suitable materials, for example, titanium or nitinol. In the preferred embodiment, titanium may be used as being more desirable than nitinol. Where titanium is used, the stent structure 104 is not generally collapsible as would be the case if constructed from nitinol. The stent portion 128 may form a support structure in the nature of, for example, a plurality of circumferentially arranged upstanding support posts 131 on which the leaflet or leaflets 130 may be secured and supported through known means, such as using sutures.

The second stent structure 104 having an interior region is adapted to be secured to the first stent structure 102, and specifically to the collar 116 within the interior region 110. The second stent structure 104 may include at least one engagement member such as a tab 132 extending radially outward, although two tabs are illustrated in FIG. 3. Each tab 132, when more than one is provided, may be formed as part of a base 134 which has a throughbore 136 for passage of blood therethrough. The base 134 may be secured to the stent portion 128, and optionally, to the at least one leaflet 130a-130c of the heart valve. Each tab 132 is adapted to fit within and be received by the first and second grooves 120, 122 or opening 126.

The tabs 132 may have any desired geometrical cross section such as square, polygonal or the like which is adapted to be engaged within the first and second grooves 120, 122 or opening 126. As shown in FIG. 3, a pair of tabs 132 may be arranged circumferentially opposing one another projecting outwardly from the base 134. In this regard, the collar 116 would be provided with a pair of spaced apart grooves 120, 122 or openings 126 for engagement with a respective one of the tabs. The second grooves 122 would be circumferentially arranged about the collar 116 so as to align with the circumferentially spaced apart tabs 132 extending from the base 134.

Figure 4:
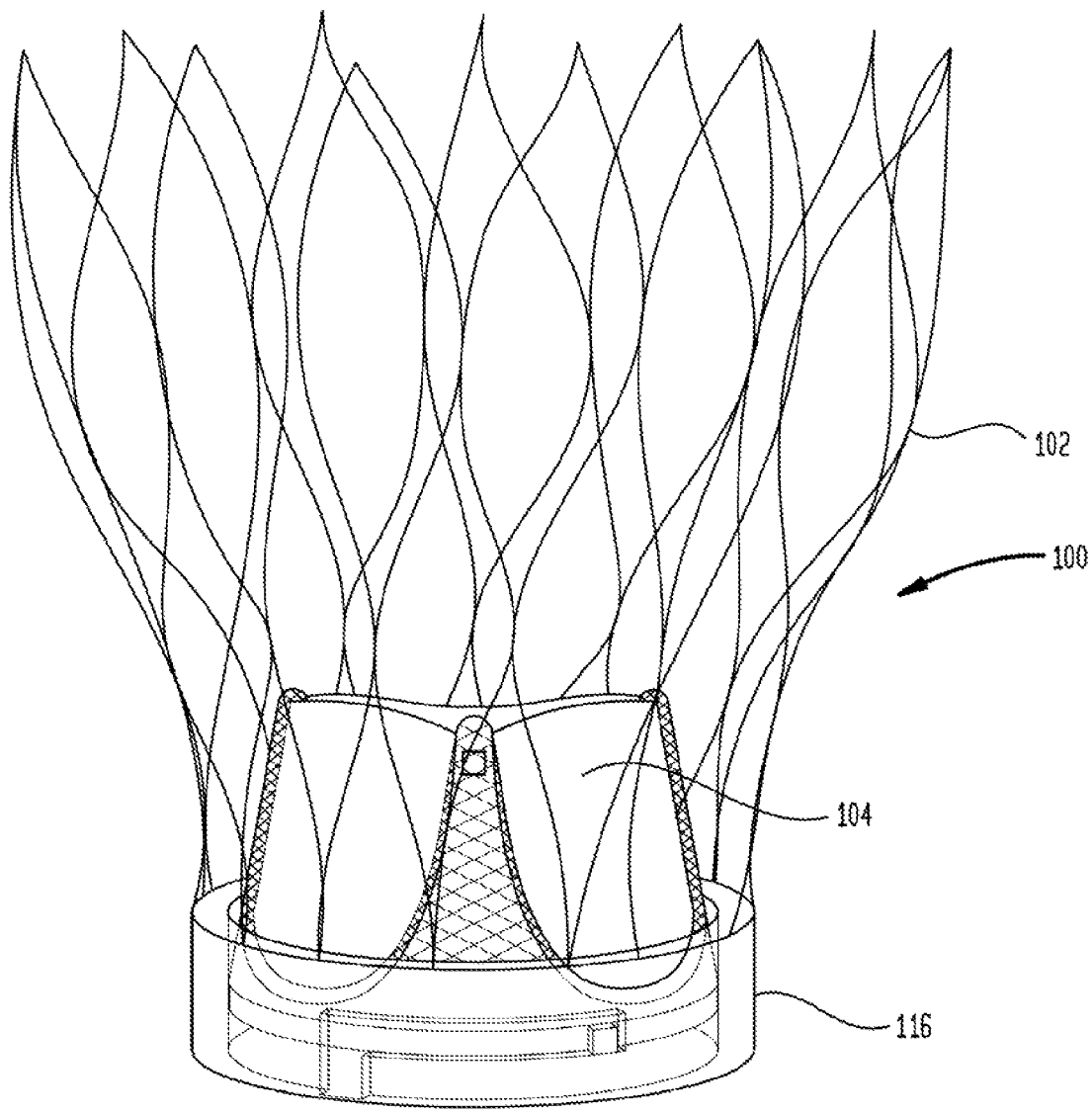
FIG. 4 is a perspective view illustrating the assembled relationship of the first and second stents thereby forming a sutureless prosthetic heart valve.

The first and second stent structures 102, 104 may be secured to one another through the interaction of the at least one tab 132 of the second stent structure 104 with the grooves 120, 122 or opening 126 of the first stent structure. The second stent structure 104 is configured to be positioned within the throughbore 118 of the first stent structure 102, such that the at least one tab 132 and second groove 122 align with one another. As the second stent structure travels into the throughbore, and along longitudinal axis 112, the tab 132 travels through the groove 122 until the tab is positioned at the intersection with the first groove 120 (see FIG. 1A). At this intersection, the second stent structure 104 is adapted to rotate relative to the first stent structure 102 such that the tab 132 now travels along the first groove 120 circumferentially. With the tab 132 received within and rotated along the first groove 120, the first and second stent structures are secured to one another as shown in FIG. 4. In the embodiment disclosed in FIG. 1B, the tab 132 is adapted to be received within the opening 126 for securing the first and second stent structures 102, 104 together in the manner as thus far described. The first and second stent structures may be releasably secured to one another in this fashion if more than one tab and more than one groove are present as described above, so long as, the multiple tabs and grooves can align with one another.

As the predominate forces on the second stent structure 104 in use are typically axial forces, the first and second stent structures remain in their locked position. It is contemplated that any tortional forces that would tend to untwist the second stent structure 104 from its locked position will be relatively small, and specifically, in comparison to the axial forces. If desired, the tabs 132 and grooves 120, 122 or opening 126 can be configured to provide a friction fit, by way of one example, to prevent the second stent structure 104 from possibly turning when implanted.

The prosthetic heart valve device 100 may be implanted using a catheter commonly used in heart valve replacement surgery. For example, the catheter for deployment of the first stent structure 102 should be capable of compressing the annular section 106, such as by the use of a sleeve surrounding the annular section, which may be removeable once the first stent structure 102 is properly positioned within the patient. The catheter for the deployment of the second stent structure 104, on the other hand, should be capable of grasping the base 134 and providing a pushing/pulling force to the stent structure, as well as a rotational force for securing the tab 132 in the groove 120 of the first stent structure 102. If the second stent structure 104 is also collapsible and expandable, the catheter should be capable of compressing and expanding the second stent structure, as required, since the second stent structure may not be self-expandable. In this case, an inflatable balloon for expanding either the first or second stent structures 102, 104 can be used as is well known in the art.

The present disclosure also includes embodiments of methods of implantation of the prosthetic heart valve devices 100 during open heart surgery on the patient. This exemplary method to be described concerns the replacement of an aortic valve, though similar methods may be used in replacing heart valves other than the aortic valve during closed heart surgical procedures.

The surgeon initially accesses the heart of the patient and places the patient on cardiopulmonary bypass. The surgeon then accesses the interior of the aorta to approach the native site of the aortic valve from the aorta. Optionally, the surgeon may then remove the native leaflets of the aortic valve.

Figure 5:
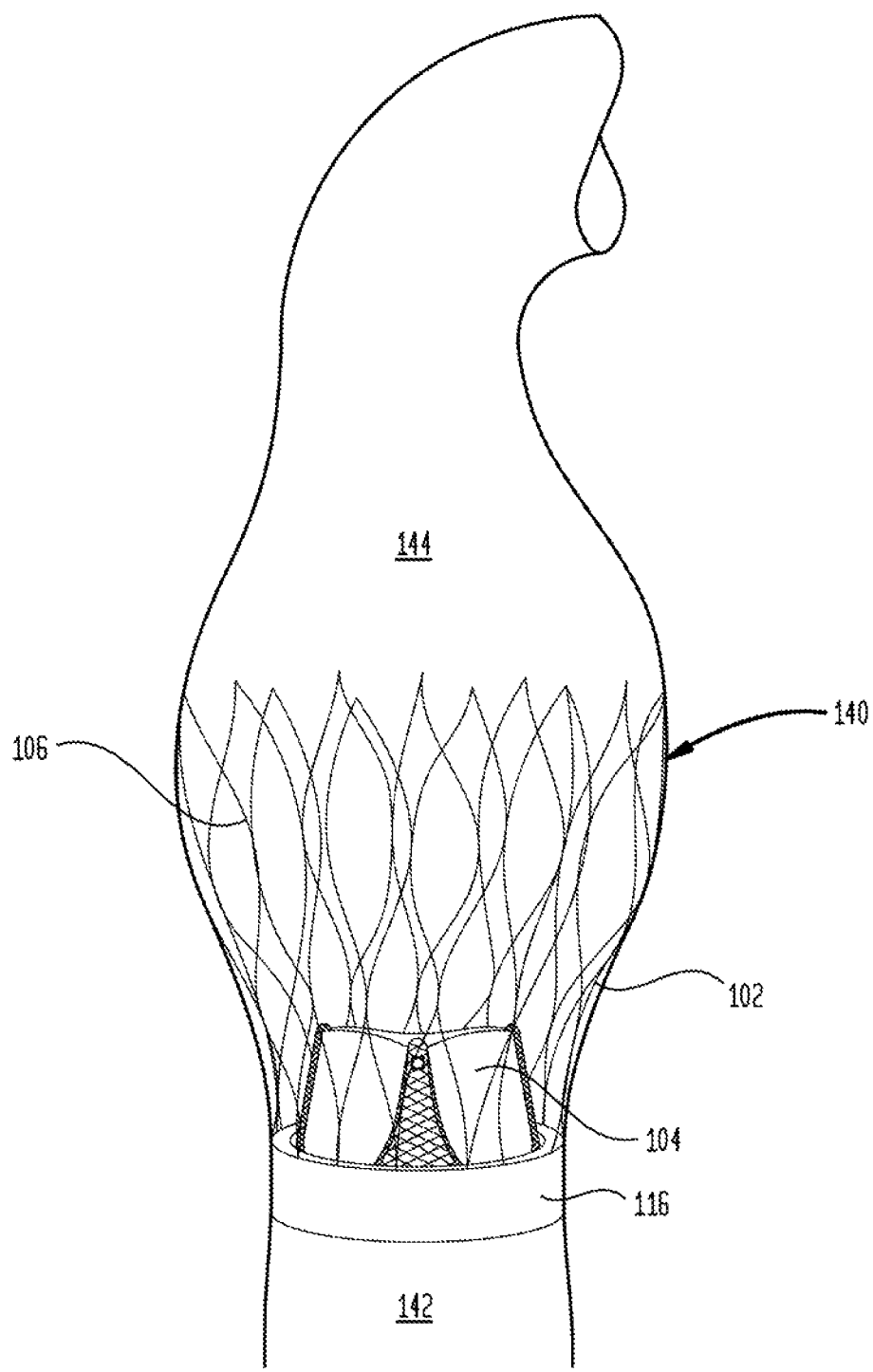
FIG. 5 is a perspective view of the prosthetic heart valve post implant in an annulus.

From the aortic approach as shown in FIG. 5, the first stent structure 102 is deployed at the native site 140 of the aortic valve. As discussed above, the first stent structure 102 may be self-expandable, and thus, upon reaching the native site, the first stent structure may be released from an insertion catheter such that it self-expands and holds itself in place without suturing. If the native leaflets were left at the native site, the first stent structure 102, upon expanding, may force the leaflets against the side walls of the vessel such that they are held open at all times. In one example, the first stent structure 102 is orientated at the native site such that the collar 116 is within the left ventricle 142, within the native annulus, or adjacent to the native annulus, and thus, the annulus section 106 extends from the collar and into the aorta 144.

Once the first stent structure 102 is secured in place, the second stent structure 104 may be deployed, also from an aortic approach, such that it is positioned within the interior region 110 of the first stent structure. The second stent structure 104 includes a replacement aortic valve 129 having a stent portion 128 supporting at least one leaflet 130. As this embodiment is for replacement of the aortic valve, the replacement valve may have three leaflets 130a, 130b, 130c as illustrated in FIG. 31. As shown in FIG. 4, the base 134 will be positioned at or adjacent to the collar 116, while the stent portion 128 extends away from the left ventricle of the heart and towards the aorta.

Finally, the second stent structure 104 may be removably secured to the first stent structure 102. As discussed above, securing the two stent structures together includes, for example, mating at least one tab 132 of the second stent structure 104 with the collar 116 of the first stent structure 102. Specifically, tab 132 may be press-fit into groove 122 until the tab is positioned at the intersection with groove 120. The second stent structure 104 may then be rotated to position the tab 132 within the opposite end of the groove 120. It should be noted that only nominal rotation is required to place the tab within the groove 120, for example, rotation is only required to be sufficient to move the tab 132 out of groove 122. Upon such rotation, the first and second stent structures form prosthetic heart valve device 100 which is now secured in place to replace the native aortic valve without the need for suturing. It is contemplated that this procedure is reversible if there is a need to remove the second stent structure without removing the first stent structure 102.

The method of implantation using the expandable or self-expanding stent structure 102 eliminates the need for the placement of sutures to secure the stent structure to the surrounding anatomy. For example, sutures are not required to secure the prosthetic heart valve device 100 to the existing valve annulus, as commonly may be required in certain procedures. Instead, the prosthetic heart valve device 100 is held in position by the expanding nature of the first stent structure 102, securely against the surrounding tissue, such as the native aortic annulus.

Alternative embodiments aside from that illustrated are also envisioned. For example, the securement structure between the first and second stent structures 102, 104 may be structures other than the at least one tab 132 and the grooves 120, 122 or opening 126. For example, matching threads on the collar 110 and the base 134 may secure the two stent structures to one another. Other alternatives may include a ratchet-like structure, a simple press-fit (e.g. a Morse taper or the like), a tab and eyelet structure, or any other combination suitable for securing the two structures to one another.

The prosthetic heart valve device 100 may provide for a quicker and more simplified procedure, which may result in a decreased period of time the patient must be placed on cardiopulmonary bypass during open heart surgery. By decreasing the amount of bypass time, the risk of complications during open heart surgery is also reduced, which results in a higher success rate and an increase in the number of patients who may undergo the procedure.

Certain aspects of the various embodiments of the disclosed device are described in the following paragraphs.

The prosthetic device may be used in an anatomical orifice or lumen of a patient, the device including a first stent structure defining an interior region and having a collar at one end thereof, a valve support structure adapted to be secured to the collar within the interior region of the first stent structure, and a valve structure coupled to the valve support structure; and/or the first stent structure being configured to be self-expandable from a collapsed state to an expanded state; and/or the valve support structure comprising a second stent structure; and/or the first and second stent structures constructed from titanium or nitronol; and/or the valve structure including a plurality of leaflets; and/or the valve support structure including an engagement member and the collar including an engagement member receiving structure; and/or the engagement member receiving structure including a longitudinal first groove in communication with a circumferential second groove adapted to receive the engagement member; and/or the engagement member comprising at least one radially projecting tab adapted to fit within first and second grooves; and/or the valve support structure comprising a second stent having a plurality of upstanding support posts coupled to the valve structure; and/or the first stent structure including a longitudinal axis through the interior region and the valve support structure adapted to be received within the interior region along the longitudinal axis opposing the collar, whereby the at least one tab is received within the first groove which is arranged parallel to the longitudinal axis, and whereby the valve support structure is adapted to be rotated around the longitudinal axis such that the at least one tab travels along the second groove in a circumferential direction relative to the longitudinal axis; and/or the valve structure comprising a heart valve; and/or the receiving structure including a longitudinal first opening in communication with a circumferential second opening adapted to receive the engagement member.

In other embodiments, the prosthetic device may be used in an anatomical orifice or lumen of a patient, the device including a first stent structure defining an interior region having a longitudinal axis, the first stent structure including a collar, the collar having at least one engagement member receiving structure, a second stent structure having at least one engagement member adapted to be received within the engagement member receiving structure of the first stent structure for releasably securing the second stent structure to the first stent structure within the interior region; and/or the engagement member receiving structure having a first portion extending parallel to the longitudinal axis and a second portion extending in a circumferential direction about the longitudinal axis; and/or the first and second portions including a groove; and/or the first and second portions including an opening; and/or further including a valve structure coupled to the second stent structure; and/or the valve structure comprising a heart valve.

In other embodiments, the sutureless prosthetic heart device includes a first stent structure defining a first interior region about a longitudinal axis, the first stent structure including a collar surrounding one end of the first stent structure, the collar including a first groove extending longitudinally to an edge of the collar in communication with a second groove extending circumferentially about the collar, wherein the first stent structure is configured to be expandable from a collapsed state to an expanded state, a second stent structure defining a second interior region, the second stent structure supporting a heart valve structure having at least one leaflet arranged within the second interior region, the second stent structure including a base having at least one tab extending radially outward therefrom, wherein the second stent structure is configured to be received within the first interior region of the first stent structure with the base juxtaposing the collar, and wherein the second stent structure is securable to the first stent structure by initially receiving the at least one tab within the first groove, and then, within the second groove of the collar by rotation of the first and second stent structures relative to one another; and/or the first and second stent structures constructed from nitinol or titanium; and/or the first stent structure configured to be self-expandable from a collapsed state to an expanded state.

In other embodiments, a method is disclosed for assembling a prosthetic device for use in an anatomical orifice or lumen of a patient, the method including arranging a valve support structure including a valve having at least one leaflet within an expandable first stent structure, the expandable first stent structure configured to be attached at a native site of an anatomical orifice or lumen of a patient, and securing the valve support structure to the first stent structure; and/or further including expanding the first stent structure from a collapsed state to an expanded state; and/or the first stent structure including a collar having a circumferential groove in communication with a longitudinal groove along an edge of the collar; and/or the valve support structure including at least one tab extending radially outward therefrom, the tab configured to be received within the circumferential and longitudinal grooves; and/or the step of securing includes mating the at least one tab of the valve support structure with the collar on the first stent structure by directing the at least one tab into the longitudinal groove, and rotating the valve support structure such that the at least one tab is directed from the longitudinal groove and into the circumferential groove; and/or arranging the valve support structure includes positioning the at least one tab juxtaposed the collar of the firs stent structure; and/or the valve support structure includes a second stent structure.

In other embodiments, the prosthetic device may be used in an anatomical orifice or lumen of a patient, the device comprising a first structure defining a first interior region expandable from a collapsed configuration to an expanded configuration, the first structure having a collar at an end thereof, and a second structure defining a second interior region, the second structure having a portion configured to be secured to the collar when the second structure is received within the first interior region when the first structure is in the expanded configuration; and/or wherein the first interior region is in fluid communication with the second interior region when the second structure is secured to the first structure; and/or wherein the first and second structures comprise stents; and/or wherein the collar includes at least one tab and the portion of the second structure includes a groove or an opening adapted to receive the at least one tab.

Although the device 100 has been described with reference to particular embodiments, it is to be understood that these embodiments are merely illustrative of the principles and applications of the present disclosure. For example, it is contemplated that the first and second stent structures 102, 104 may be pre-assembled prior to implantation. In this regard, it is contemplated that the prosthetic heart valve device 100 could be collapsible for implantation using a catheter. Further, it is contemplated that the device described hereinabove may be used in general in an anatomical orifice or lumen of a patient for treatment of other bodily conditions of the patient. It is therefore to be understood that numerous modifications may be made to the illustrative embodiments and that other arrangements may be devised without departing from the spirit and scope of the present invention as defined by the appended claims.

The invention claimed is:

1. A prosthetic device for use in an anatomical orifice or lumen of a patient, the device comprising:
    a first stent structure constructed from a plurality of struts having free ends and configured to form a plurality of cells defining an interior region, a collar encircling the first stent structure attached to the free ends of the plurality of struts and having a throughbore, the collar including an engagement member receiving structure;
    a valve support structure comprising a second stent structure having a base at an end thereof and adapted to be secured to the collar within the interior region of the first stent structure, the valve support structure including an engagement member provided on the base; wherein the engagement member receiving structure comprises a longitudinal first groove in communication with a circumferential second groove adapted to receive the engagement member, and the engagement member comprises at least one radially projecting tab adapted to fit within the first and second grooves; and
    a valve structure coupled to the valve support structure,
    wherein the first stent structure includes a longitudinal axis through the interior region, the valve support structure configured to be received through the throughbore of the collar and within the interior region along the longitudinal axis with the collar juxtaposing the base, whereby the at least one tab is received within the first groove which is arranged parallel to the longitudinal axis, and whereby the valve support structure is configured to be rotated around the longitudinal axis such that the at least one tab travels along the second groove in a circumferential direction relative to the longitudinal axis.

2. The device of claim 1, wherein the first stent structure is configured to be self-expandable from a collapsed state to an expanded state.

3. The device of claim 2, wherein the first and second stent structures are constructed from titanium or nitinol.

4. The device of claim 1, wherein the valve structure includes a plurality of leaflets.

5. The device of claim 1, wherein the second stent has a plurality of upstanding support posts coupled to the valve structure.

6. The device of claim 1, wherein the valve structure comprises a heart valve.

7. A prosthetic device for use in an anatomical orifice or lumen of a patient, the device comprising:
a first stent structure constructed from a plurality of struts having free ends and configured to form a plurality of cells defining an interior region having a longitudinal axis, the first stent structure including a collar having a throughbore attached to the free ends of the plurality of struts, the collar encircling the first stent structure and having at least one engagement member receiving structure provided on the collar, wherein the at least one engagement member receiving structure has a first portion extending parallel to the longitudinal axis and a second portion extending in a circumferential direction about the longitudinal axis;
a second stent structure having an end provided with a base having a throughbore, at least one engagement member protruding from the base and adapted to be received within the engagement member receiving structure on the collar of the first stent structure for releasably securing the second stent structure to the first stent structure within the interior region, wherein the throughbore of the collar is aligned with the throughbore of the base when the second strut structure is received within the interior region of the first stent structure with the collar juxtaposed the base, whereby the engagement member is secured within the at least one engagement member receiving structure by rotation therebetween.

8. The device of claim 7, wherein the first and second portions comprise a groove.

9. The device of claim 7, wherein the first and second portions comprise an opening.

10. The device of claim 7, further including a valve structure coupled to the second stent structure.

11. The device of claim 10, wherein the valve structure comprises a heart valve.

12. A sutureless prosthetic heart valve device comprising:
constructed from a plurality of struts having free ends and configured to form a plurality of cells defining a first interior region about a longitudinal axis, the first stent structure including a collar attached thereto and encircling the free ends of the plurality of struts surrounding one end of the first stent structure, the collar having a throughbore and including a first groove extending longitudinally to an edge of the collar in communication with a second groove extending circumferentially about the collar, wherein the first stent structure is configured to be expandable from a collapsed state to an expanded state;
a second stent structure defining a second interior region, the second stent structure supporting a heart valve structure having at least one leaflet arranged within the second interior region, the second stent structure including a base forming a throughbore and having at least one tab extending radially outward therefrom;
wherein the second stent structure is configured to be received within the first interior region of the first stent structure with the base juxtaposing the collar, wherein the throughbore of the collar is aligned with the throughbore of the base when the second strut structure is received within the interior region of the first stent structure; and
wherein the second stent structure is securable to the first stent structure by initially receiving the at least one tab within the first groove, and then, within the second groove of the collar by rotation of the first and second stent structures relative to one another.

13. The device of claim 12, wherein the first and second stent structures are constructed from nitinol or titanium.

14. The device of claim 12, wherein the first stent structure is configured to be self-expandable from a collapsed state to an expanded state.

15. A prosthetic device for use in an anatomical orifice or lumen of a patient, the device comprising:
a first stent structure constructed from a plurality of struts having free ends and configured to form a plurality of cells defining a first interior region, the first structure having a collar attached to and encircling the free ends of the plurality of struts, the collar having at least one engagement member receiving structure; and
a second stent structure defining a second interior region and expandable from a collapsed configuration to an expanded configuration, the second structure having an end provided with a base having a throughbore, the base having a portion configured to be secured to the collar by the at least one engagement member receiving structure when the second structure is received within the first interior region when the first structure is in the expanded configuration,
wherein the throughbore of the collar is aligned with the throughbore of the base when the second strut structure is received within the interior region of the first stent structure with the collar juxtaposed the base.

16. The device of claim 15, wherein the first interior region is in fluid communication with the second interior region when the second structure is secured to the first structure.

17. The device of claim 16, wherein the portion of the base comprises at least one tab and the at least one engagement member receiving structure of the first structure includes a groove or an opening adapted to receive the at least one tab.

* * * * *